(12) United States Patent
Stansbury et al.

(10) Patent No.: US 8,883,948 B2
(45) Date of Patent: Nov. 11, 2014

(54) METHODS FOR EXTENSIVE DARK CURING BASED ON VISIBLE-LIGHT INITIATED, CONTROLLED RADICAL POLYMERIZATION

(75) Inventors: Jeffrey W. Stansbury, Aurora, CO (US); Dongkwan Kim, Broomfield, CO (US)

(73) Assignee: The Regents of the University of Colorado, Denver, CO (US)

( * ) Notice: Subject to any disclaimer, the term of this patent is extended or adjusted under 35 U.S.C. 154(b) by 117 days.

(21) Appl. No.: 13/001,535

(22) PCT Filed: Jul. 1, 2009

(86) PCT No.: PCT/US2009/049454
§ 371 (c)(1),
(2), (4) Date: Mar. 16, 2011

(87) PCT Pub. No.: WO2010/003026
PCT Pub. Date: Jan. 7, 2010

(65) Prior Publication Data
US 2011/0166306 A1 Jul. 7, 2011

Related U.S. Application Data

(60) Provisional application No. 61/077,337, filed on Jul. 1, 2008.

(51) Int. Cl.

| | | |
|---|---|---|
| C08F 2/00 | (2006.01) | |
| C08F 4/00 | (2006.01) | |
| C08F 220/10 | (2006.01) | |
| C08F 4/42 | (2006.01) | |
| C08F 120/10 | (2006.01) | |
| C08F 20/10 | (2006.01) | |
| A61K 6/083 | (2006.01) | |
| A61K 6/00 | (2006.01) | |
| A61C 5/04 | (2006.01) | |
| A61C 13/00 | (2006.01) | |
| A61C 13/08 | (2006.01) | |

(52) U.S. Cl.
CPC .............. A61K 6/083 (2013.01); A61K 6/0017 (2013.01); A61K 6/0023 (2013.01); A61C 5/04 (2013.01); A61C 13/0003 (2013.01); A61C 13/08 (2013.01)
USPC ............. 526/318; 526/89; 526/183; 526/211; 526/217

(58) Field of Classification Search
USPC ............................ 526/89, 183, 211, 217, 318
See application file for complete search history.

(56) References Cited

U.S. PATENT DOCUMENTS

| | | | |
|---|---|---|---|
| 3,729,313 A | 4/1973 | Smith | |
| 3,741,769 A | 6/1973 | Smith | |
| 3,808,006 A | 4/1974 | Smith | |
| 4,250,053 A | 2/1981 | Smith | |
| 4,394,403 A | 7/1983 | Smith | |
| 4,503,169 A | 3/1985 | Randklev | |
| 4,642,126 A | 2/1987 | Zador et al. | |
| 4,652,274 A | 3/1987 | Boettcher et al. | |
| 4,695,251 A | 9/1987 | Randklev | |
| 4,735,632 A | 4/1988 | Oxman et al. | |
| 4,828,583 A | 5/1989 | Oxman et al. | |
| 4,868,092 A | 9/1989 | Kawabata et al. | |
| 5,229,253 A | 7/1993 | Zertani et al. | |
| 5,998,495 A | 12/1999 | Oxman et al. | |
| 6,017,660 A | 1/2000 | Palazzotto et al. | |
| 6,025,406 A | 2/2000 | Oxman et al. | |
| 6,043,295 A | 3/2000 | Oxman et al. | |
| 6,953,829 B2 * | 10/2005 | Kratzer et al. | ............... 526/160 |
| 2005/0009946 A1 | 1/2005 | Oguri et al. | |
| 2005/0136210 A1 * | 6/2005 | Boettcher | ...................... 428/76 |
| 2006/0189728 A1 | 8/2006 | Qian | |
| 2008/0096150 A1 | 4/2008 | Cinader | |

FOREIGN PATENT DOCUMENTS

| | | |
|---|---|---|
| DE | 3918105 | 12/1989 |
| EP | 0014293 | 8/1980 |
| EP | 0382209 | 8/1990 |
| JP | H02-127404 | 5/1990 |

OTHER PUBLICATIONS

Chesneau et al. "Polymérisation induite sous irradiation laser visible. 2. Sensibilisation par les colorants," Die Angewandte Makromolekulare Chemie, Oct. 1985, vol. 135, No. 1, pp. 41-64.

Kawabata et al. "Properties of Dye-sensitized Polymer Containing Pendant N-Phenylglycine Moiety," Journal of Photopolymer Science and Technology, 1990, vol. 3, No. 2, pp. 147-148.

Valdes-Aguilera et al. "Photopolymerization studies using visible light photoinitiators" Macromolecules, Jan. 1992, vol. 25, No. 2, pp. 541-547.

Kumar et al. "Laser-induced three-dimensional photopolymerization using visible initiators and UV cross-linking by photosensitive comonomers," Macromolecules, Jul. 1991, vol. 24, No. 15, pp. 4322-4327.

Bi et al. "A Visible Light Initiating System for Free Radical Promoted Cationic Polymerization," Macromolecules, Jul. 1994, vol. 27, No. 14, pp. 3683-3693.

Fouassier et al. "Visible light-induced polymerization reactions: The seven-role of the electron transfer process in the dye/iron arene complex/amine system," Journal of Applied Polymer Science, Dec. 1996, vol. 62, No. 11, pp. 1877-1885.

Erddalane et al. "Efficiency and excited state processes in a three-component system, based on thioxanthene derived dye/amine/additive, usable in photopolymer plates," Journal of Polymer Science Part A: Polymer Chemistry, Mar. 1996, vol. 34, No. 4, pp. 633-642.

(Continued)

Primary Examiner — Karuna P Reddy
(74) Attorney, Agent, or Firm — Sheridan Ross P.C.

(57) ABSTRACT

Optimized methods to achieve extensive dark curing from a three-component visible light-initiated system though controlled radical polymerization and compositions useful in these optimized methods are provided. These compositions and methods are particularly suited for use in certain dental applications.

7 Claims, 17 Drawing Sheets

(56) References Cited

OTHER PUBLICATIONS

Padon et al. "A mechanistic investigation of a three-component radical photoinitiator system comprising methylene blue, N-methyldiethanolamine, and diphenyliodonium chloride," Journal of Polymer Science Part A: Polymer Chemistry, Jun. 1, 2000, vol. 38, No. 11, pp. 2057-2066.

Kim et al. "The role of diphenyl iodonium salt (DPI) in three-component photoinitiator systems containing methylene blue (MB) and an electron donor," Journal of Polymer Science Part A: Polymer Chemistry, Dec. 1, 2004, vol. 42, No. 23, pp. 5863-5871.

Lalevee et al. "Controlled photopolymerization reactions: The reactivity of new photoiniferters," Journal of Polymer Science Part A: Polymer Chemistry, Jun. 15, 2007, vol. 45, No. 12, pp. 2436-2442.

Kilambi et al. "Copolymerization and dark polymerization studies for photopolymerization of novel acrylic monomers," Polymer, Mar. 13, 2007, vol. 48, No. 7, pp. 2014-2021.

Padon et al. "Spectroscopic Investigation of Three-Component Initiator Systems," ACS Symposium Series, vol. 847, Photoinitiated Polymerization, Chapter 2, pp. 15-26, Mar. 3, 2003.

Padon et al. "Recent Advances in Three Component Photoinitiator Systems," Recent Research Development in Polymer Science, vol. 3, 1999, pp. 369-385.

International Search Report for International (PCT) Patent Application No. PCT/US09/49454, mailed Aug. 14, 2009 4 pages.

Written Opinion for International (PCT) Patent Application No. PCT/US09/49454, mailed Aug. 14, 2009 5 pages.

International Preliminary Report on Patentability for International (PCT) Patent Application No. PCT/US2009/049454, mailed Jan. 13, 2011 7 pages.

* cited by examiner

METHODS FOR EXTENSIVE DARK CURING BASED ON VISIBLE-LIGHT INITIATED, CONTROLLED RADICAL POLYMERIZATION

CROSS REFERENCE TO RELATED APPLICATION

This application is a national stage application under 35 U.S.C. 371 of PCT Application No. PCT/US2009/049454 having an international filing date of Jul. 1, 2009, which designated the United States, which PCT application claimed the benefit of U.S. Application Ser. No. 61/077,337, filed Jul. 1, 2008, the entire disclosure of each of which is hereby incorporated herein by reference.

GOVERNMENT RIGHTS

This invention was made with government support under grant number R21 DE018354 awarded by the National Institutes of Health. The government has certain rights in the invention.

TECHNICAL FIELD

This invention relates to optimized methods to achieve extensive dark curing from a three component visible-light initiated system though controlled radical polymerization.

BACKGROUND OF INVENTION

Free-radical photopolymerization has been used to prepare polymetric materials including films, adhesives, coatings and composites. The process has the advantages of low energy demand, rapid and readily controllable reaction kinetics, excellent mechanical properties and the versatility available with a broad array of monomers. It has been reported that visible light activated three-component initiator systems (utilizing a photosensitizer, an electron acceptor, and an electron donor) produce enhanced rates of polymerization, higher sensitivity and higher conversions than the visible light-activated two-component initiator systems that include a photosensitizer and an electron donor (Chesneau, E., Fouassier, J. P.; Angew. Makromol Chem. (1985), 135, 41; Kawabata M.; Takimoto, Y.; J. Photpolymer Sci Technol. (1991) 3, 147; Hoechst, A. G.; Japan Kokai (1990), 02, 127,404; Kumar, G. S.; Neckers, D. C., Marcomolecules (1991) 24, 4322; Fouassier, J. P., Morlet-Savary, F R.; Yamashita, K.; Imahashi, S., J. of Applied Polymer Science (1996) 62, 1877). Several effective three-component initiator systems have also been reported (U.S. Pat. No. 4,735,632, U.S. Pat. No. 4,828,583, U.S. Pat. No. 6,017,660, U.S. Pat. No. 6,043,295).

Radical-based photopolymerization is characterized by a rapid cessation of polymerization when the photo-curing light source is extinguished. To maintain the active polymerization to completion, continuous initiation is required because radical based active centers have short propagating times due to highly efficient termination reactions. In contrast, cationic photopolymerization allows significant dark curing because of long active center lifetimes. But, compared with radical polymerizations, there are few monomers compatible with the cationic curing process. This dark curing behavior is one of the distinct differences between cationic and free-radical photopolymerization, and the prospect of removing this dark cure limitation from radical-based polymerizations with conventional monomers is highly significant because effective dark curing would be useful to reduce processing times and lower initiator concentrations. as well as to achieve photo-curing in shadow regions, enhancing the depths of cure and for photo-curing pigmented or highly-filled systems using radical polymerizations.

There are few examples of free-radically polymerizable monomers that exhibit considerable dark cure potential (Kilambi, H.; Reddy, S. K.; Schneidewind, L; Stanswbury, J. W.; Bowman, C. N. *Copolymerization and dark polymerization studies for photopolymerization of novel acrylic monomers.* Polymer (2007) 48: 2014-2021). These are (meth)acrylate monomers that are characterized by a number of unusual properties such as hyper-reactivity and significant formation of crosslinks from mono-vinyl polymerization in addition to substantial dark cure potential with conventional photo-initiating systems. However, these monomers are not commercially available and their unique behavior is dramatically different from that of conventional (meth)acrylate monomers, such as HEMA and HEA, that are more frequently used in polymerization reactions.

Therefore, there remains a need in the art for a method for extensive dark curing from a visible-light initiated controlled radical polymerization of commonly used monomers.

SUMMARY OF THE INVENTION

The present invention provides a composition and a method for extensive dark curing from a visible-light initiated controlled radical polymerization in which the radical active centers are not terminated even when the light source is extinguished.

The invention provides methods and compositions for dark curing of polymerizable compositions. One embodiment of the invention is a composition prepared for dark curing that includes a monomer with at least one abstractable hydrogen, and a three-component initiator system, soluble in the monomer. The three-component initiator system of this embodiment is a composition containing a photo-oxidizable photosensitizing agent, an electron donor, and an electron acceptor.

In preferred aspects of this embodiment, the monomer may include 2-hydroxyethyl acrylate (HEA), 2-hydroxyethyl methacrylate(HEMA), acrylamide, methacrylamide, bis-GMA {2,2-bis[4-(2-hydroxy-3-methacryloxyprop-1-oxy)phenyl]propane}, urethane dimethacrylate, glycerol monomethacrylate, 1,3, glycerol dimethacrylate, tetrahydrofurfuryl methacrylate, 1,6-hexanediol diacrylate, 1,6-hexanediol dimethacrylate (HDDA), methacrylic acid, triethylene glycol dimethacrylate, styrene, neodecyl vinyl ester, or combinations thereof.

In preferred aspects of this embodiment, the photosensitizing agent may include safranin O, eosin Y disodium salt, fluorescein sodium salt, erythrosin B sodium salt, acriflavine, camphorquinone, methylene blue, 1-Phenyl-1,2-propanedione, acridine orange, resorufin, resazurin, phenosafranin, rose bengal, rhodamine B, thioxanthen-9-one or combinations thereof.

In preferred aspects of this embodiment, the electron donor may include triethanolamine, 4-dimethylaminophenethyl alcohol, ethyl 4-dimethylaminobenzoate, quinuclidine, N,N-diisopropyl-3-pentylamine, N-Phenylglycine, N-ethyldiisopropylamine, N-methyldiethanolamine, triethylamine (TEA), N,N-dimethylacetamide, 1,4-diazabicyclo[2.2.2]octane, 4-dimethylaminobenzaldehyde, N,N-dimethylbenzylamine, 4-tert-butyl-N,N-dimethylaniline, 9,10-dimethylanthracene, N,N-dimethylbenzylamine, 1,2,2,6,6-pentamethylpiperidine or combinations thereof.

In preferred aspects of this embodiment, the electron acceptor may include ferrocenium hexafluorophosphate, diphenyliodonium hexafluoroarsenate, [4-[(2-hydroxytetradecyl)oxyl]phenyl]phenyliodonium hexafluoroantimonate, diphenyliodonium hexafluorophosphate, 2,4,6-tris(trifluoromethyl)-1,3,5-triazine, diphenyl iodonium chloride, diphenyl iodonium tetrafluoroborate or combinations thereof.

Another embodiment of the invention is a dark curing polymerizable dental composition that contains a monomer with at least one abstractable hydrogen, a three-component initiator system, soluble in the monomer, that contains a photo-oxidizable photosensitizing agent, an electron donor, and an electron acceptor.

Another embodiment of the invention is a method of dark curing polymerization, by dissolving a photosensitizing agent, electron donor, and electron acceptor in a monomer solution. Polymerization of the resulting composition is initiating using a visible-light source. The polymerization proceeds to cure under dark conditions.

One preferred embodiment is a dark curing polymerizable composition that contains $4.122\times10^{-2}$ mol. (neat) of 2-hydroxyethyl methacrylate, a three-component initiator system, dissolved in said 2-hydroxyethyl methacrylate, that contains 0.075 mol % methylene blue; 2.5 mol % N-ethyldiisopropylamine; and 0.5 mol % diphenyliodonium chloride.

Another preferred embodiment is a dark curing polymerizable composition containing $4.122\times10^{-2}$ mol. (neat) of 2-hydroxyethyl acrylate, a three-component initiator system, dissolved in said 2-hydroxyethyl methacrylate, that contains 0.015 mol % methylene blue, 3.0 mol % N-ethyldiisopropylamine; and 0.25 mol % diphenyliodonium chloride.

DETAILED DESCRIPTION OF THE INVENTION

Figure 1:
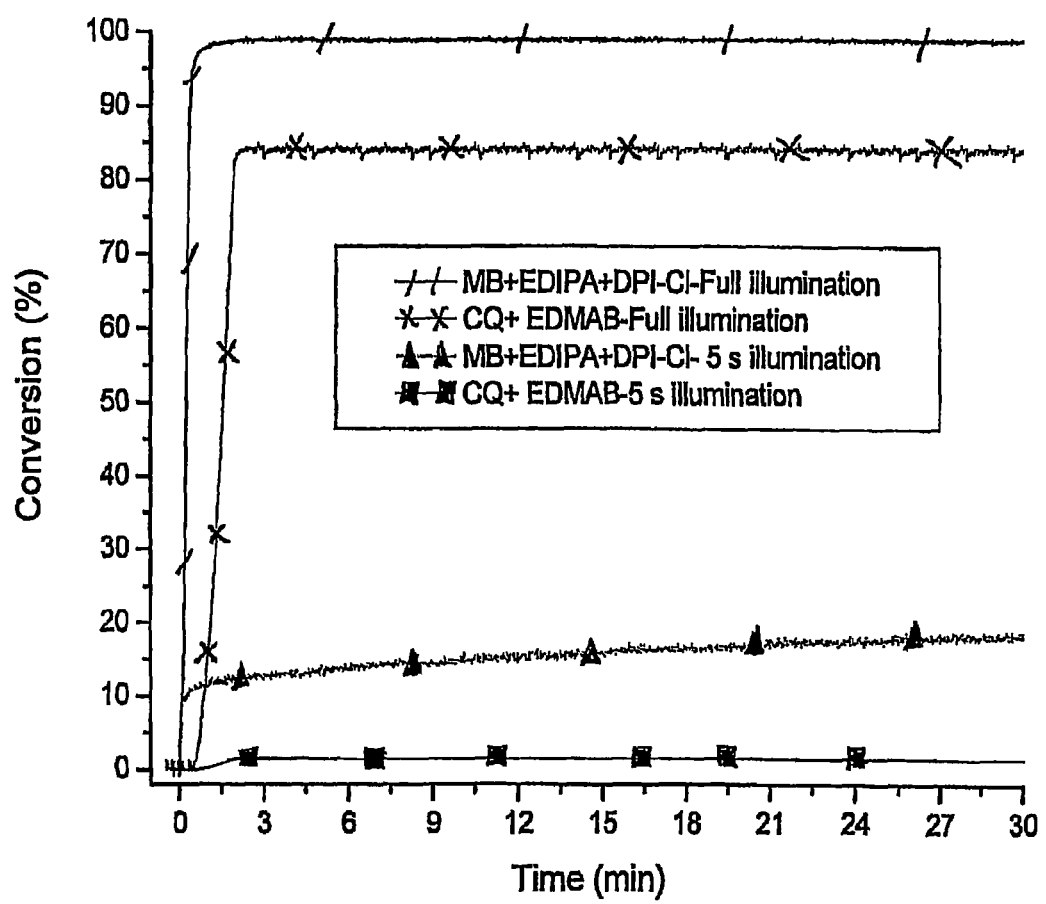
FIG. 1 illustrates the radical dark polymerization of two and three-component initiator systems.

As used herein, the following definitions shall apply unless otherwise indicated. The phrase "visible light" refers to light having a wavelength of about 400 to 1000 nanometers (nm). The term "initiation" refers to subjecting the composition to a visible-light source for a given period of time. The phrase "radical polymerization" refers to polymerization in which the reactive center of the polymer chain is a radical. The phrase "dark curing" refers to continued polymerization after the visible-light source has been removed, i.e., the radical active center is not immediately terminated when the visible-light source is removed.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that (contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl," "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I. The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members.

The term "aryl" may be used interchangeably with the term "aryl ring". The term "aralkyl" refers to an alkyl group substituted by an aryl. The term "aralkoxy" refers to an alkoxy group substituted by an aryl. The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl," used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl. An aryl (including aralkyl, aralkoxy, aryloxyalkyl and the like) or heteroaryl (including heteroaralkyl, heteroarylalkoxy and the like) group may contain one or more substituents. Suitable substituents on an unsaturated carbon atom of an aryl, heteroaryl, aralkyl or heteroaralkylgroup are selected from halogen; haloalkyl; —$CF_3$; —R; —OR; —SR; 1,2-methylenedioxy; 1,2-ethylenedioxy; protected OH (such as acyloxy); phenyl (Ph); Ph substituted with R; —O(Ph); —O-(Ph) substituted with R; $CH_2$(Ph); —$CH_2$(Ph) substituted with R; —CH2CH2(Ph); —CH2CH2(Ph) substituted with R; —$NO_2$; —CN; —$N(R)_2$; —NRC(O)R; —NRC(O)$N(R)_2$; —NRCO2R; —NRNRC(O)R; —NR—NRC(O)N(R)2; —NRNRCO2R; —C(O)C(O)R; —C(O)$CH_2$C(O)R; —$CO_{2R}$; —C(O)R; —C(O)N$(R)_2$; —OC(0)N$(R)_2$; —S$(O)_2$R; —$SO_2$N$(R)_2$; —S(O)R; —NRSO2N$(R)_2$; —NRSO2R; —C(=S)N$(R)_2$; —C(=NH)—N$(R)_2$; —($CH_2$)J, NHC(O)R; —(CH2)J, R; —(CH2)J, NHC(O)NHR; —(CH2)J, NHC(O)OR; —($CH_2$)$_y$, NHS(O)R; —(CH2)$_y$, NHSO2R; or —(CH2)J, NHC0)CH((V)z-R)(R) wherein each R is independently selected from hydrogen, optionally substituted $C_{1-6}$ aliphatic, an unsubstituted 5-6 membered heteroaryl or heterocyclic ring, phenyl (Ph), —O(Ph), or —CH2(Ph)-CH2(Ph), wherein y is 0-6; z is 0-1; and V is a linker group. When R is $C_{1-6}$ aliphatic, it may be substituted with one or more substituents selected from —$NH_2$, —NH($C_{1-4}$ aliphatic), —N($C_{1-4}$ aliphatic)$_2$-S(O)($C_{1-4}$ aliphatic), —$SO_2$($C_{1-4}$ aliphatic), halogen, ($C_{1-4}$ aliphatic), —OH, —O—($C_{1-4}$ aliphatic), —$NO_2$, —CN, —$CO_2$H, —$CO_2$($C_{1-4}$ aliphatic), —O(halo $C_{1-4}$ aliphatic), or -halo($C_{1-4}$ aliphatic); wherein each $C_{1-4}$ aliphatic is unsubstituted.

An aliphatic group or a non-aromatic heterocyclic ring may contain one or more substituents. Suitable substituents on a saturated carbon of an aliphatic group or of a nonaromatic heterocyclic ring are selected from those listed above for the unsaturated carbon of an aryl or heteroaryl group and the following: =O, =S, =NNHR, =NN$(R)_2$, =N—, =NNHC(0)R, =NNHCO$_2$(alkyl), =NNHSO$_2$ (alkyl), or =NR, where each R is independently selected from hydrogen or an optionally substituted $C_{1-4}$ aliphatic. When R is $C_{1-4}$ aliphatic, it may be substituted with one or more substituents selected from —$NH_2$, —NH($C_{1-4}$ aliphatic), —N($C_{1-4}$ aliphatic)$_2$, halogen, —OH, —O—($C_{1-4}$ aliphatic), —$NO_2$, —CN, —$CO_2$H, —$CO_2$($C_{1-4}$ aliphatic), —O(halo $C_{1-4}$ aliphatic), or -halo($C_{1-4}$ aliphatic); wherein each $C_{1-4}$ aliphatic is unsubstituted.

A wide variety of monomers can be polymerized using the three-component initiator system for controlled radical dark polymerization of the present invention. Suitable monomers contain at least one ethylenically-unsaturated double bond, may be oligomers, and are capable of undergoing addition polymerization. Such monomers include mono-, di- or polyacrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimetbacrylate, 1,3-propanediol diacrylate, 1,3-propanediol dimetbacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p propoxyphenyldimethylmethane, trishydroxyethylisocyanurate trimethacrylate; the bis-acrylates and bis-methacrylates of polyethylene glycols of molecular weight 200-500, copolymerizable mixtures of acrylated monomers such as those of U.S. Pat. No. 4,652,274, and acrylated oligomers such as those of U.S. Pat. No. 4,642,126; unsaturated amides such as methylene bis-acrylamide, methylene bis-methacrylamide, 1,6-hexamethylene bis-acrylamide, diethylene triamine tris-acrylamide and beta-methacrylaminoethyl methacrylate; and vinyl compounds such as styrene, diallyl phthalate, divinyl succinate, divinyl adipate and divinylphthalate. Mixtures of two or more monomers may also be used if desired.

In a preferred embodiment, the monomer has at least one abstractable hydrogen. Such monomers include 2-hydroxyethyl acrylate (HEA), 2-hydroxyethyl methacrylate(HEMA), acrylamide, methacrylamide, bisGMA {2,2-bis[4-(2-hydroxy-3-methacryloxyprop-1-oxy)phenyl]propane}, urethane dimethacrylate, glycerol monomethacrylate, 1,3, glycerol dimethacrylate, tetrahydrofurfuryl methacrylate, 1,6-hexanediol diacrylate, 1,6-hexanediol dimethacrylate (HDDA), methacrylic acid, triethylene glycol dimethacrylate, styrene and neodecyl vinyl ester.

The monomer is combined with a three-component or ternary photoinitiator system. The first component in the photoinitiator system is the electron acceptor. The electron acceptor should be soluble in the monomer and preferably is shelf-stable (i.e., does not spontaneously promote polymerization) when dissolved in the sensitizer and/or electron donor. Accordingly, selection of a particular electron donor may depend, to some extent, upon the particular monomer, sensitizer and donor chosen. In one embodiment, the electron donor is an iodonium salt. Suitable iodonium salts are described in U.S. Pat. Nos. 3,729,313; 3,741,769; 3,808,006; 4,250,053; and 4,394,403, the disclosures of which are incorporated herein by reference. The iodonium salt may be a simple salt (e.g., containing an anion such as Cl$^-$, Br$^-$, I$^-$ or $C_4H_5SO_3^-$) or a metal complex salt (e.g., containing SbF$_5$OH$^-$ or AsF$_6^-$). In a preferred embodiment, the electron acceptor has a large counterion. Mixtures of iodonium salts may also be used if desired.

In another embodiment, the electron acceptor is at least one of ferrocenium hexafluorophosphate, diphenyliodonium hexafluoroarsenate, [4-[(2-hydroxytetradecyl)oxyl]phenyl] phenyliodonium hexafluoroantimonate, diphenyliodonium hexafluorophosphate, 2,4,6-tris(trifluoromethyl)-1,3,5-triazine, diphenyl iodonium chloride, and diphenyl iodonium tetrafluoroborate.

The second component in the photoinitiator system is the sensitizer. The sensitizer is preferably soluble in the monomer and is capable of light absorption within the wavelengths of light between about 300 nanometers and about 1000 nanometers, more preferably between about 400 nanometers and about 700 nanometers and most preferably about 400 nanometers and about 600 nanometers. The sensitizer is also capable of sensitizing 2-methyl-4,6-bis(trichloromethyl)-s-triazine, using the test procedure described in U.S. Pat. No. 3,729,313. Using available materials, that test is carried out as follows:

A standard test solution is prepared having the following composition:

5.0 parts of a 5% (weight by volume) solution in methanol of 45,000-55,000 molecular weight, 9.0-13.0% hydroxy content polyvinyl butyral (Butvar™ B76, Monsanto), 0.3 parts trimethylolpropane trimethacrylate, 0.03 parts 2-methyl-4,6-bis(trichloromethyl)-s-triazine.

To this solution is added 0.01 parts of the compound to be tested as a sensitizer. The solution is knife-coated onto a 0.05 mm clear polyester film using a knife orifice of 0.05 mm, and the coating is air dried for about 30 minutes. A 0.05 mm clear polyester cover film is carefully placed over the dried but soft and tacky coating with minimum entrapment of air. The resulting sandwich construction is then exposed for three minutes to 161,000 Lux of incident light from a tungsten light source providing light in both the visible and ultraviolet range ("FCH" 650 watt quartz-iodine lamp, General Electric).

Exposure is made through a stencil so as to provide exposed and unexposed areas in the construction. After exposure, the cover film is removed and the coating is treated with a finely divided colored powder, such as a color toner powder of the type conventionally used in xerography. If the tested compound is a sensitizer, the trimethylolpropane trimethacrylate monomer will be polymerized by the light exposed areas by the light-generated free radicals from the 2-methyl-4,6-bis(trichloromethyl)-s-triazine. Since the polymerized areas will be essentially tack-free, the colored powder will selectively adhere only to the tacky, unexposed areas of the coating, providing a visual image corresponding to that in the stencil.

Preferably, in addition to passing the above test, a sensitizer is also selected based in part upon shelf stability. Accordingly, selection of a particular sensitizer may depend, to some extent, upon the particular monomer, electron acceptor and electron donor chosen.

Suitable sensitizers may include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity (e.g., graphic arts), it is preferred to employ a sensitizer containing a julolidinyl moiety.

By way of example, a preferred class of ketone sensitizers has the formula:

where X is CO or $CR^1R^2$ where $R^1$ and $R^2$ can be the same different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin, and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-mdolylethanedione, 2,3-bomanedione (camphorquinone), biacetyl, 1,2-cyclohexanedione, 1,2-naphthaquinone, acenaphthaquinone, and the like.

In a preferred embodiment, the photosensitizer is photo-oxidizable. In another preferred embodiment, the photosensitizer is chosen from the group consisting of safranin O, eosin Y disodium salt, fluorescein sodium salt, erythrosin B sodium salt, acriflavine, camphorquinone, methylene blue (MB), 1-Phenyl-1,2-propanedione, acridine orange, resorufin, resazurin, phenosafranin, rose bengal, rhodamine B, thioxanthen-9-one.

The third component in the photoinitiator system is the electron donor. A wide variety of donors can be employed. The donor is soluble in the monomer, and should meet the oxidation potential ($E_{ox}$) limitation discussed in more detail below. Preferably, the donor also is selected based, in part, upon shelf stability. Accordingly, a selection of a particular donor may depend in part on the monomer, electron acceptor and photosensitizer chosen. Also, the donor has an $E_{ox}$ greater than zero and less than or equal to $E_{ox}$ (p-dimethoxybenzene). Preferably $E_{ox}$ (donor) is between about 0.5 and 1 volts vs. a saturated calomel electrode ("S.C.E."). $E_{ox}$ (donor) values can be measured experimentally, or obtained from references such as N. L. Weinburg, Ed., Technique of Electroorganic Synthesis Part II Techniques of Chemistry, Vol. V (1975), and C. K. Mann and K. K. Barnes, Electrochemical Reactions in Nonaqueous Systems (1970). Preferred electron donors have high radical cation persistence.

Suitable electron donors include amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents.

Preferred amine donor compounds include alkyl-, aryl-, alkaryl- and aralkyl-amines such as methylamine, ethylamine, propylamine, butylamine, triethanolamine, amylamine, hexylamine, 2,4-dimethylaniline, 2,3-dimethylaniline, o-, m- and p-toluidine, benzylamine, aminopyridine, N,N'-dimethylethylenediamine, N,N'-diethylethylenediamine, N,N'-dibenzylethylenediamine, N,N'-diethyl-1,3- propanediamine, N,N'-diethyl-2-butene-1,4-diamine, N,N'-dimethyl-1,6-hexanediainine, piperazine, 4,4'-trimethylenedipiperidine, 4,4'-ethylenedipiperidine, p-N N-dimethyl-aminophenethanol and p-N-dimethylamxnobenzonitrile; aminoaldehydes such as p-N,N-dimethylaminobenzaldehyde, p-N,N-diethylaminobenzaldehyde, 9-julolidine carboxaldehyde and 4-morpholinobenzaldehyde; and aminosilanes such as trimethylsilylmorpholine, trimethylsilylpiperidine, bis(dimethylamino)diphenylsilane, tris(dimethylamino)methylsilane, N,N-diethylaminotrimethylsilane, tris(dimethylamino)phenylsilane, tris(methylsilyl)amine, tris(dimethylsilyl)amine, bis(dimethylsilyl)amine, N,N-bis(dimethylsilyl)aniline, N-phenyl-Ndimethylsilylaniline and N,N-dimethyl-Ndimethylsilylamine. Tertiary aromatic alkylamines, particularly those having at least one electron-withdrawing group on the aromatic ring, have been found to provide especially good shelf stability. Good shelf stability has also been obtained using amines that are solids at room temperature.

Preferred amide donor compounds include N,N-dimethylacetamide, N,N-diethylacetamide, N-methyl-N-phenylacetamide, hexamethylphosphoramide, hexaethylphosphoramide, hexapropylphosphoramide, trimorpholinophosphine oxide. tripiperidinophosphine oxide and mixtures thereof.

Suitable ether donor compounds include 4,4'-dimethoxybiphenyl, 1,2,4-trimethoxybenzene and 1,2,4,5-tetramethoxybenzene. Suitable urea donor compounds include N,N'-dimethylurea, N,N-dimethylurea, N,N'-diphenylurea, tetramethylthiourea, tetraethylthiourea, tetra-n-butylthiourea, N,N-di-nbutylthiourea, N,N'-di-n-butylthiourea, N,Ndiphenylthiourea, N,N'-diphenyl-N,N'-diethylthiourea and mixtures thereof.

In a preferred embodiment, the electron donor is chosen from the group consisting of triethanolamine, 4-dimethylaminophenethyl alcohol, ethyl 4-dimethylaminobenzoate, quinuclidine, N,N-diisopropyl-3-pentylamine, N-Phenylglycine, N-ethyldiisopropylamine, N-methyldiethanolamine, triethylamine (TEA), N,N-dimethylacetamide, 1,4-diazabicyclo[2.2.2]octane, 4-dimethylaminobenzaldehyde, N,N-dimethylbenzylamine, 4-tert-butyl-N,N-dimethylaniline, 9,10-dimethylanthracene, N,N-dimethylbenzylamine, 1,2,2,6,6-pentamethylpiperidine.

The three components of the photoinitiator system are present in "effective amounts," that is, amounts of each component sufficient to enable the monomer to undergo photochemical initiation upon exposure to light of the desired wavelength for a specified time and continue to polymerize when the irradiation source is turned off. The amounts of each component are independently variable and thus need not be equal, with larger amounts generally providing faster cure, but shorter shelf life.

The compositions of the invention can contain a wide variety of adjuvants depending upon the desired use of the formed polymer. Suitable adjuvants include solvents, diluents, resins, binders, plasticizers, pigments, dyes, inorganic or organic reinforcing or extending fillers (at preferred amounts of about 10% to about 90% by weight, based on the total weight of the composition), thixotropic agents, indicators, inhibitors, stabilizers, UV absorbers, medicaments (e.g., leachable fluorides) and the like. The amounts and types of such adjuvants, and their manner of addition to a composition of the invention will be familiar to those skilled in the art.

The compositions of the invention can be initiated using a variety of visible-light sources. In one embodiment, a halogen lamp can be used as a visible light source. In another embodiment, a modified dental curing light can be used as a visible light source. In one embodiment of this invention, the composition is initiated with a visible-light source for about 10 seconds to about 60 minutes.

Dental applications particularly benefit from the unique compositions of the present invention. Until now, acrylate and methacrylate chemistry has been used extensively for adhesive and restorative dental compositions. This chemistry has the disadvantage of being curable only with continued exposure to visible light. In contrast, during polymerization in the compositions of the present invention, polymerization continues after the light-source has been removed allowing for extensive dark curing. The present invention provides a system for dark curing polymerizable monomers in an acceptable time frame and to a sufficient depth using a visible light source-initiated three-component system and equipment already available in the dental office. The dental materials may be filled or unfilled and include dental materials such as direct esthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein refers to a filled dental material. The term "restorative" as used herein refers to a composite which is polymerized after it is disposed adjacent to a tooth. The term "prosthesis" as used herein refers to a composite which is shaped and polymerized for its final use (e.g., as crown, bridge, veneer, inlay, onlay or the like) before it is disposed adjacent to a tooth. The term "sealant" as used herein refers to a lightly filled composite or to an unfilled dental material which is cured after it is disposed adjacent to a tooth. "Polymerizable" refers to curing or hardening the dental material, e.g., by a free radical mechanism.

In certain applications, the use of a filler may be appropriate. The choice of filler affects important properties of the composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Dark curing polymerizable compositions of the invention, either alone or in a mixture with a diluent monomer, can be prepared with refractive indices which approach or approximate the refractive indices of fillers such as quartz (refractive index 1.55) submicron silica (refractive index 1.46), and 5.5:1 mole ratio SiO:ZrO, non-vitreous microparticles (refractive index 1.54). In this way, the appearance of the dental material can, if desired, be made to closely approximate the appearance of natural dentition.

Radiopacity is a measurement of the ability of the composite to be detected by x-ray examination. Frequently a radiopaque composite will be desirable, for instance, to enable the dentist to determine whether or not a dental restoration remains sound. Under other circumstances a non-radiopaque composite may be desirable.

The amount of filler which is incorporated into the composite, referred to herein as the "loading level" and expressed as a weight percent based on the total weight of the dental material, will vary depending on the type of filler, the epoxy resin and other components of the composition, and the end use of the composite.

For some dental materials, such as sealants, the epoxy resin compositions of the invention can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 70 and 90 weight percent is generally preferred.

Fillers may be selected from one or more of any material suitable for incorporation in compositions used for medical applications, such as fillers currently used in dental restorative compositions and the like. The filler is finely divided and preferably has a maximum particle diameter of less than about 50 micrometers and an average particle diameter of less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filter. The filler should in any event be non-toxic and suitable for use in the mouth. The filler can be radiopaque, radiolucent or nonradiopaque.

Examples of suitable inorganic fillers are naturally occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the Aerosil™ Series "OX 50", "130", "150" and "200" silicas sold by Degussa and Cab-O-Sil™ M5 silica sold by Cabot Corp.). Examples of suitable organic filler particles include filled or unfilled pulverized polycarbonates, poly epoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof.

Conventional dental amalgam alloy powders, typically mixtures of silver, tin, copper, and zinc may optionally be incorporated. The particulate metallic filler preferably has an average particle size of about 1 micron to about 100 microns, more preferably about 1 micron to about 50 microns. Mixtures of these fillers are also contemplated, as well as combination fillers made from organic and inorganic materials. Fluoro aluminosilicate glass fillers, either untreated or silanol treated, are particularly preferred. These glass fillers have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like. Examples of coupling agents include silanes such as gamma-methacryl oxypropyl trimethoxysilane, Gamma-mercapto propyl triethoxysilane, beta-(3,4-epoxycyclohexyl)ethyl-trimethoxy silane, gamma glycid oxypropyl trimethoxysilane, and the like.

The materials of the present invention can also contain suitable adjuvants such as accelerators, inhibitors, absorbers, stabilizers, pigments, dyes, viscosity modifiers, surface tension depressants and wetting aids, antioxidants, and other ingredients well known to those skilled in the art.

The amounts and types of each ingredient in the dental material should be adjusted to provide the desired physical and handling properties before and after cure. For example, the cure rate, cure stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

When the dental material is applied to a tooth, the tooth can optionally be pre-treated with a primer such as dentin or enamel adhesive by methods known to those skilled in the art.

The invention is further described by reference to the following examples, which are understood to be merely illustrative and not limiting of the invention.

EXAMPLES

Example 1

Comparisons: Commercial Two-Component Initiator System (CQ/EDMAB) vs. Three-Component Initiator Systems (MB+EDIPA+DPI-Cl)

FIG. 1 illustrates the radical dark polymerizations of two and three-component initiator systems: MB+EDIPA+DPI-Cl vs. CQ+EDMAB. The figure shows the conversions of HEA dark polymerizations using two and three-component initiator systems comparisons with 5 second illumination: as measured by NIR at room temperature with an incident light intensity of 500 mW/cm$^2$ is shown. For all samples, [MB]=[CQ]=0.05 mol %, [EDIPA]=[EDMAB]=1.5 mol % and [DPI-Cl]=0.25 mol % in neat HEA (4.122×10$^{-2}$ mol).

The organic dyes methylene blue (MB), Camphorquinone (CQ), Zinc tetraphenylporphyrin (Zn-tpp) and rose benbal (RB)) were used as received from Chemical Company. Table 1 illustrates chemical structures of the photosensitizers (PS). Triethylamine (TEA), N-ethyldiisopropylamine (EDIPIBA) and N,N-diisopropylisobutylamine (DIPA) were used as electron donors (DH). Table 2 illustrates chemical structures of the electron donors. Diphenyliodonium chloride (DPI-Cl) and Diphenyliodonium hexafluorophosphate (DPI-PF$_6$) were used as electron acceptors (EA). Diphenyliodonium hexafluoroarsenate (DPI-AsF$_6$) was used as received from TCI America. Table 3 illustrates chemical structures of the electron acceptors. The monomer 2-hydroxyethyl methacrylate (HEMA) and 2-hydroxyethyl acrylate (HEA) were used as received from Aldrich.

TABLE 1

| Photosensitizer | Chemical Structure | $E_{red}$ (eV. SCE) | $E_t$ (kJ/mol) | $\lambda_{max}$ (nm) |
|---|---|---|---|---|
| Methylene blue (MB) | 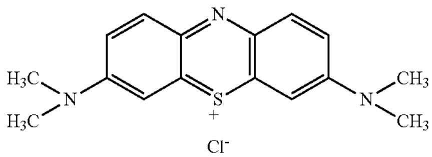 | −0.32 | 138 | 656 |
| Camphorquinone (CQ) | 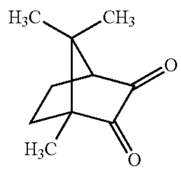 | −1.25 | 211 | 468 |
| Zinc tetraphenylporphyrin (Zn-tpp) | 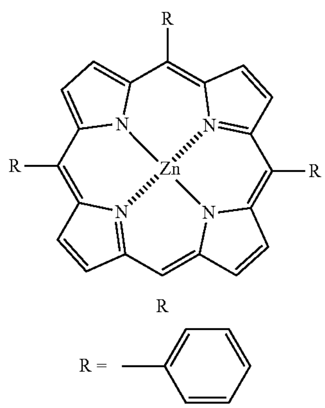 | −1.35 | 153 | 560 |
| Rose Bengal (RB) | 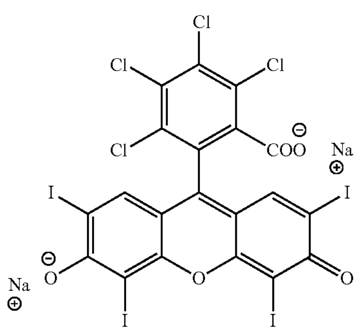 | −0.95 | 175 | 548 |
| Resazurin (RZ) | 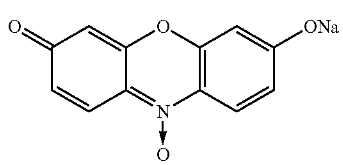 | | | |
| Resorufin (RF) | 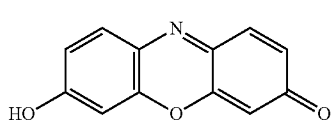 [SMILES: O=c1ccc2nc3ccc(O)cc3oc-2c1] | | | |

TABLE 2

Electron donors (DH) for three-component initiator systems

| Electron Donor | Chemical Structure | $E_{ox}$(V. SCE) |
|---|---|---|
| Triethylamine (TEA) | [structure] | 0.97 |
| N-ethyldiisopropylamine (EDIPA) | [structure] | 0.68 |
| N,N-diisopropyl-3-pentylamine (DIPA) | [structure] | 0.72 |

TABLE 3

Electron acceptors (EA) for three-component initiator systems

| Third Component | Chemical Structure | $E_{red}$(V. SCE) |
|---|---|---|
| Diphenyliodonium chloride (DPI-Cl) | [structure] | −0.20 |
| Diphenyliodonium chloride (DPI-PF$_6$) | [structure] | −0.20 |
| Diphenyliodonium chloride (DPI-AsF$_6$) | [structure] | −0.20 |
| Triphenylsulphonium Chloride (TPS) | [structure] | −1.20 |

Formulations

The dye, MB (0.015 mol %), an electron donor (3.0 mol %) and an electron acceptor (0.25 mol %) dissolved completely upon addition to the monomer (HEMA, 4.122×10$^{-2}$ mol) or (HEA, 4.122×10$^{-2}$ mol) for 30 minutes using a vibration mixer at room temperature. After completely mixing the three-component initiators in a monomer, the formulation was directly used for controlled radical dark polymerizations.

| Formulation 1 | | | |
|---|---|---|---|
| Components | MW (g/mol) | Composition | Weight (g) |
| HEMA | 130.14 | 4.122 × 10$^{-2}$ mol | 5.3644 |
| Methylene blue (MB) | 373.9 | 0.015 mol % | 0.0023 |
| EDIPA | 129.25 | 3.0 mol % | 0.1598 |
| DPI-Cl | 316.57 | 0.25 mol % | 0.0326 |

| Formulation 2 | | | |
|---|---|---|---|
| Components | MW (g/mol) | Composition | Weight (g) |
| HEMA | 130.14 | 4.122 × 10$^{-2}$ mol | 5.3644 |
| Methylene blue (MB) | 373.9 | 0.075 mol % | 0.0115 |
| EDIPA | 129.25 | 0.5 mol % | 0.0266 |
| DPI-Cl | 316.57 | 0.50 mol % | 0.0652 |

| Formulation 3 | | | |
|---|---|---|---|
| Components | MW (g/mol) | Composition | Weight (g) |
| HEMA | 130.14 | 4.122 × 10$^{-2}$ mol | 5.3644 |
| Methylene blue (MB) | 373.9 | 0.075 mol % | 0.0115 |
| EDIPA | 129.25 | 2.5 mol % | 0.1330 |
| DPI-Cl | 316.57 | 0.50 mol % | 0.0652 |

Light Sources

In this study, two visible light sources (halogen lamp for low intensity experiments and modified dental curing light for high intensity experiments) were used. First, a 100 W quartz halogen lamp for low intensity experiments was used as the photoinitiating light source for the polymerization kinetics measurements. To initiate photopolymerizations, a 385 nm to 800 nm light source (Oriel Model 77501 Fiber Optics Source, Stratford, Conn.) was used. The visible light source contains an adjustable iris, a manual shutter and a 100 W quartz halogen lamp outfitted with 3.2 mm diameter and 0.9 m length silica fiber optic cable. The output from the light source was passed through IR blocking filter to remove IR light (wavelengths greater than 800 nm). The filtered light irradiance reaching the sample was ~0.15 mW/cm$^2$, as measured by a calibrated diode array spectrometer.

The second light source is a modified dental curing light (Coltolux 75) with an effective wavelength of between 350 and 800 nm. This light source was used to activate polymerizations monitored by FT-near-infrared (NIR) spectroscopy. The incident irradiance provided by the dental light was ~500 mW/cm$^2$ as measured by a calibrated diode array spectrometer. For these light sources, 2-inch diameter glass filter (Oriel Instruments, model #59472) was used to remove below 400 nm wavelength of the emission of the light source.

Real-Time FT-Near-Infrared (NIR) Spectroscopy

The HEMA or HEA polymerization conversion profile was monitored at room temperature in situ by FT-near-infrared (NIR) spectroscopy (Nicolet Nexus 670, Nicolet Instrument Corp., Madison, Wis.) equipped with an extended KBr beamsplitter and an MCT/A detector. To initiate photopolymerizations, a 385 nm to 800 nm light source (Oriel Model 77501 Fiber Optics Source, Stratford, Conn.) for low intensity (~0.15 mW/cm$^2$) experiments or modified dental curing light for high intensity (~500 mW/cm$^2$) experiments was used. For the complete dark polymerizations, a glass filter 2-inch diameter glass filter (Oriel Instruments, model #59560) was used to remove IR emission wavelength of the IR laser in the FT-near-infrared (NIR) spectroscopy. For this experiment, white light in the FT-near-infrared (NIR) spectroscopy turned off and IR light turned on and used for characterization. Samples with a variety of photoinitiator compositions were prepared in a rectangular mold made by glass slides at a thickness of 0.5 mm to exclude oxygen in the real-time NIR experiments. The absorbance peak area method was used to calculate conversion. The =$CH_2$ first overtone absorption band at approximately 6167 $cm^{-1}$ in the NIR region was used to characterize the concentration of the HEMA or HEA double bond at room temperature.

Figure 2:
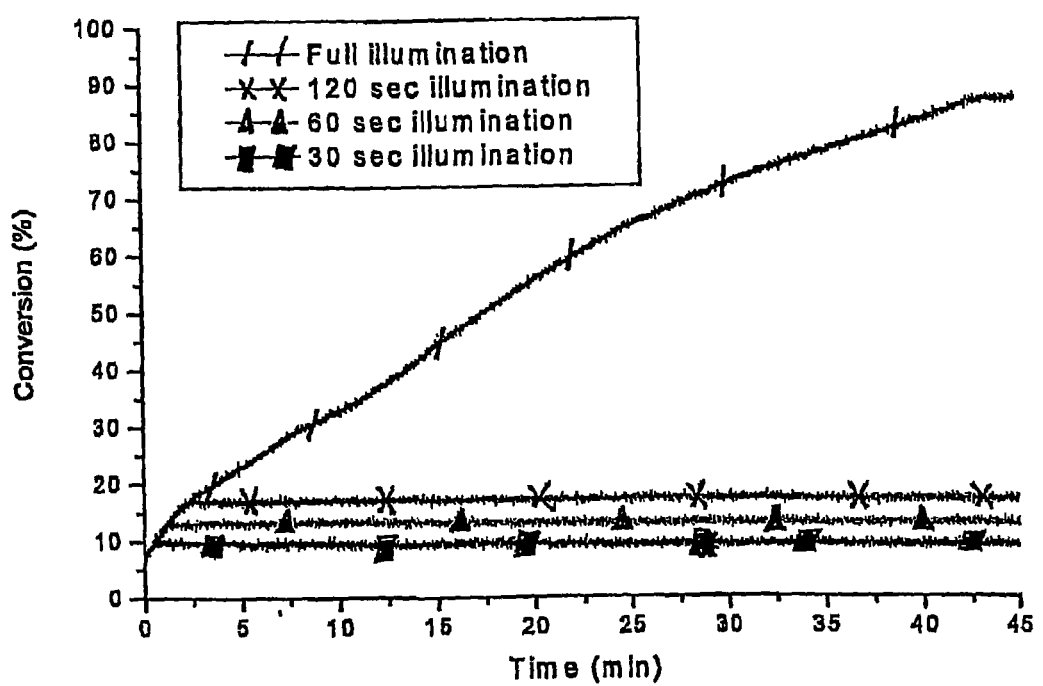
FIG. 2 illustrates the polymerization system used as a negative control in the studies described herein.

FIG. 2 illustrates the negative control system. Conversions of HEA polymerizations as a function of illumination time with MB/TEA, as measured by NIR at room temperature with an incident light intensity of 500 $mW/cm^2$ is shown. For all samples, [MB]=0.015 mol %, [TEA]=3.0 mol %, in neat HEA (4.122×$10^{-2}$ mol).

Figure 3:
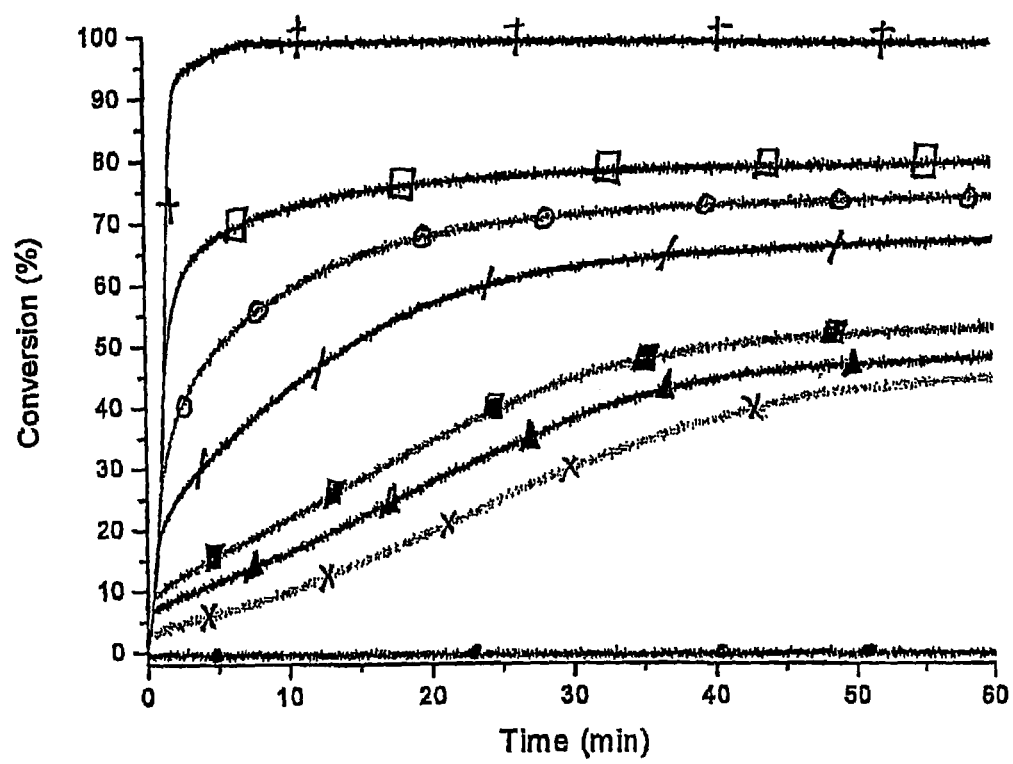
FIGS. 3-5 illustrate positive control polymerization systems used in the studies described herein.

FIG. 3 illustrates the first positive control system. Conversions of HEMA polymerizations as a function of illumination time, 60 min, 76 s, 65 s, 50 s, 30 s, 20 s, 10 s 0 s, with MB/EDIPIBA/DPI-Cl, as measured by NIR at room temperature with an incident light intensity of 0.15 $mW/cm^2$ is shown. For all samples, [MB]=0.075 mol %, [EDIPA]=2.5 mol %, and [DPI-Cl]=0.50 mol % in neat HEMA (4.122×$10^{-2}$ mol).

TABLE 4

Radical Dark HEMA Polymerizations: Conversions of HEMA polymerizations as a function of illumination time with formulation 3 For all samples, [MB] = 0.075 mol %, [EDIPA] = 2.5 mol %, and [DPI-Cl] = 0.50 mol % in neat HEMA (4.122 × $10^{-2}$ mol).

| Illumination Time (s) | Initial Conversion (%) | Final Conversion (%) |
|---|---|---|
| 76 | 43.3 | 80.0 |
| 65 | 23.8 | 74.4 |
| 50 | 17.2 | 67.4 |
| 30 | 8.6 | 52.5 |
| 20 | 6.1 | 48.1 |
| 10 | 1.3 | 44.6 |
| 0 | 0.0 | 0.0 |

Figure 4:
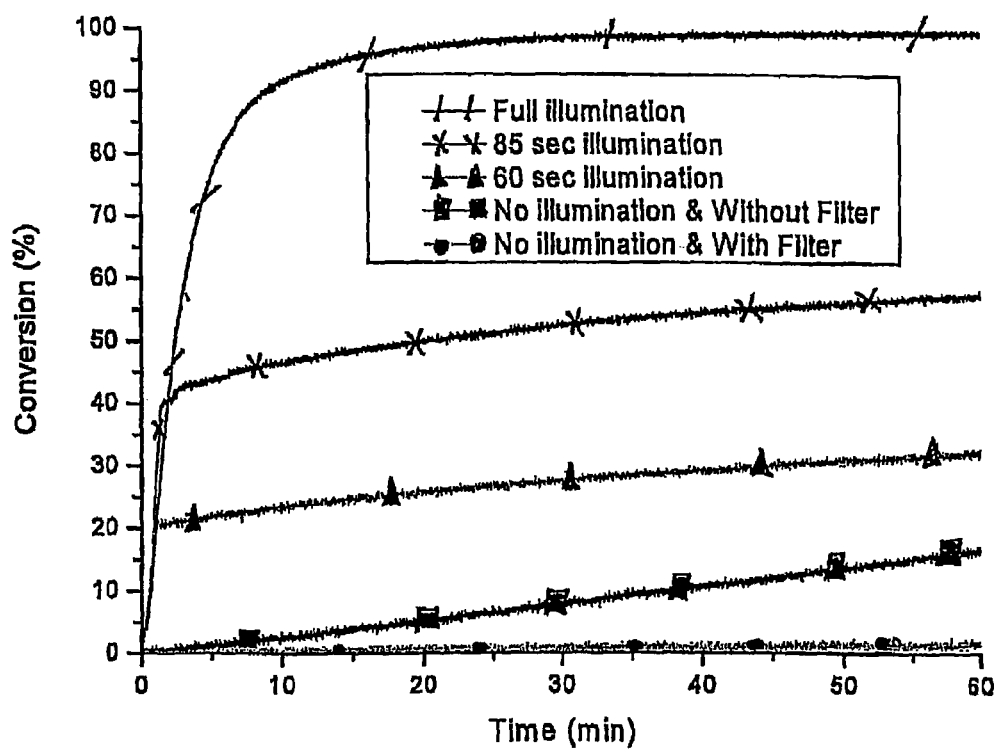

FIG. 4 illustrates the second positive control system. Conversions of HEA polymerizations as a function of illumination time with MB/EDIPA/DPI-Cl, as measured by NIR at room temperature with an incident light intensity of 0.15 $mW/cm^2$ is shown. For all samples, [MB]=0.015 mol %, [EDIPIBA]=3.0 mol %, and [DPI-Cl]=0.25 mol % in neat HEA (4.122×$10^{-2}$ mol).

Figure 5:
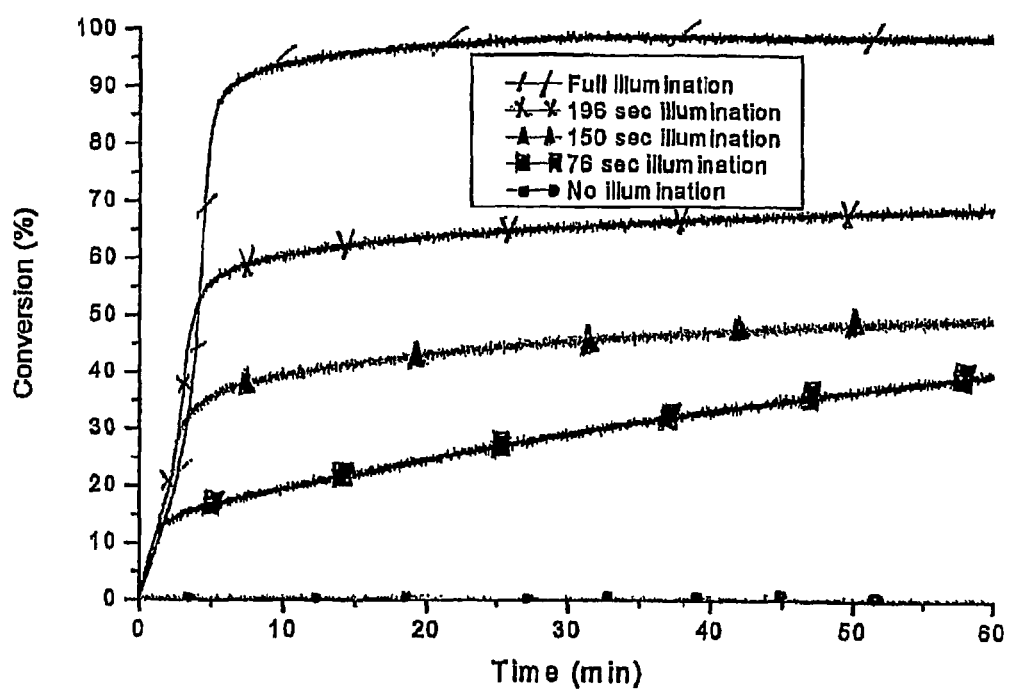

FIG. 5 illustrates the third positive control system. Conversions of HEMA polymerizations as a function of illumination time with MB/EDIPIBA/DPI-Cl, as measured by NIR at room temperature with an incident light intensity of 500 $mW/cm^2$ is shown. For all samples, [MB]=0.015 mol %, [EDIPIBA]=3.0 mol %, and [DPI-Cl]=~0.25 mol % in neat HEMA (4.122×$10^{-2}$ mol).

Example 2

Radical Dark Polymerizations: Effects of the Photosensitizer

Figure 6:
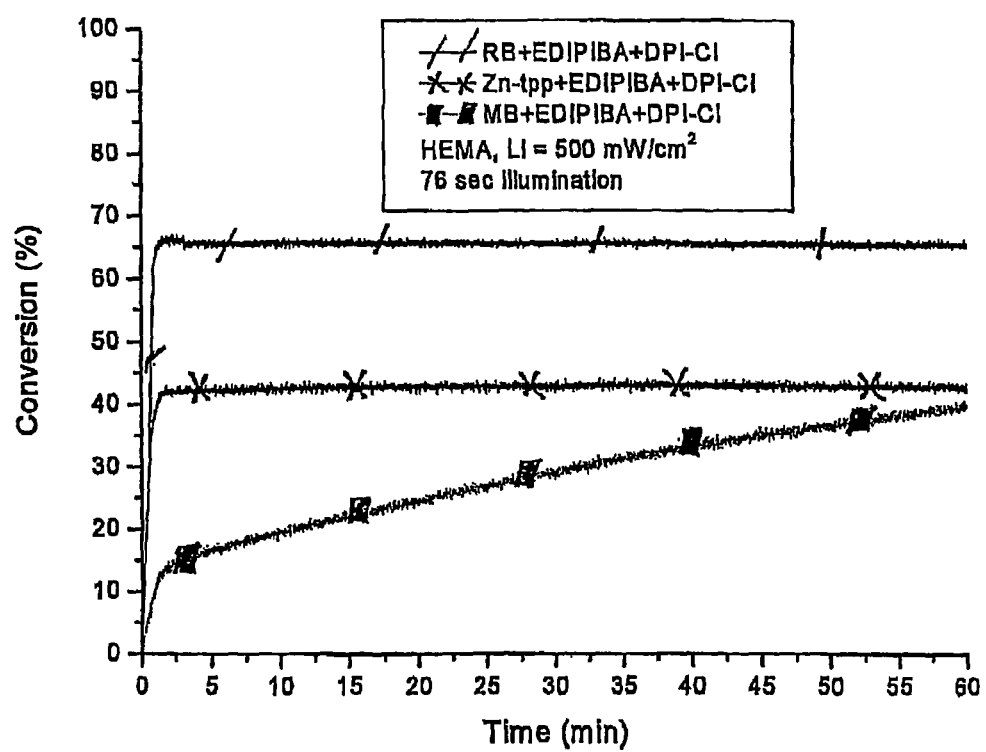
FIG. 6 illustrates the effect of varying the photosensitizer on polymerizable compositions of the present invention.

FIG. 6 illustrates the effect of varying the photosensitizer. Conversions of HEMA polymerizations as a function of illumination time with PS/EDIPA/DPI-Cl, as measured by NIR at room temperature with an incident light intensity of 500 $mW/cm^2$ is shown. For all samples, [PS]=0.015 mol %, [EDIPA]=3.0 mol %, and [DPI-Cl]=0.25 mol % in neat HEMA (4.122×$10^{-2}$ mol).

Figure 7:
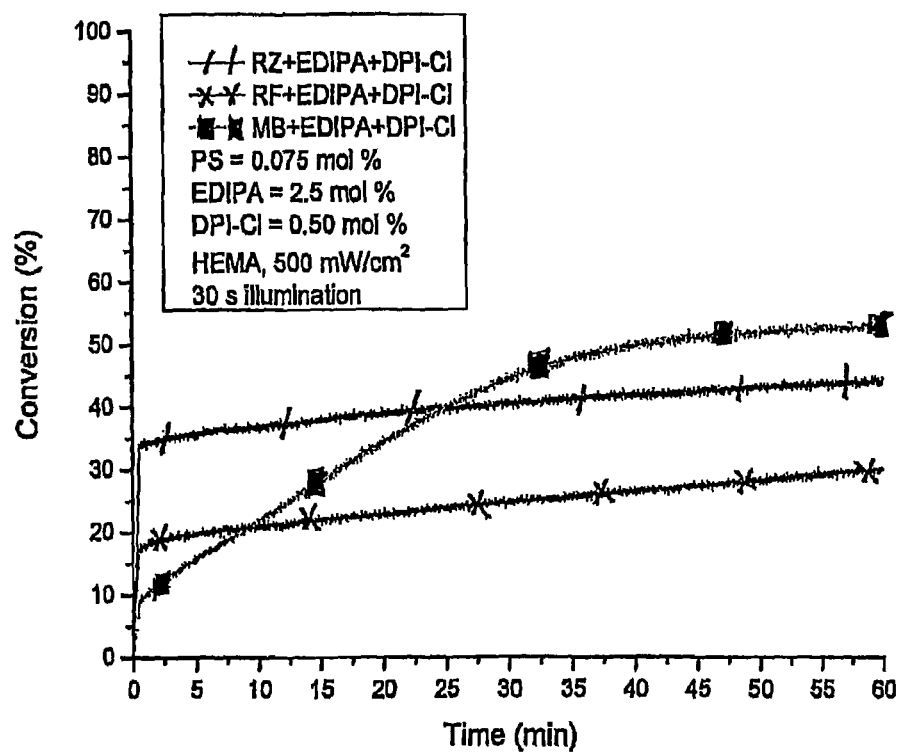
FIG. 7 illustrates the conversions of HEMA polymerizations as a function of illumination time.

FIG. 7 illustrates the conversions of HEMA polymerizations as a function of illumination time with PS/EDIPA/DPI-Cl, as measured by NIR at room temperature with an incident light intensity of 500 $mW/cm^2$ and 30 seconds illumination time. For all samples, [PS]=0.075 mol %, and [EDIPA]=2.50 mol %, and [DPI-Cl]=0.50 mol % in neat HEMA (4.122×$10^{-2}$ mol).

TABLE 5

Radical Dark HEMA Polymerizations: Conversions of HEMA with 30 second illumination time. For all samples, [PS] = 0.075 mol %, [EDIPA] = 2.5 mol %, and [DPI-Cl] = 0.50 mol % in neat HEMA (4.122 × $10^{-2}$ mol).

| PS | Initial Conversion (%) | Final Conversion (%) |
|---|---|---|
| RZ | 32.6 | 44.6 |
| RF | 17.3 | 30.0 |
| MB | 8.6 | 52.5 |

Figure 8:
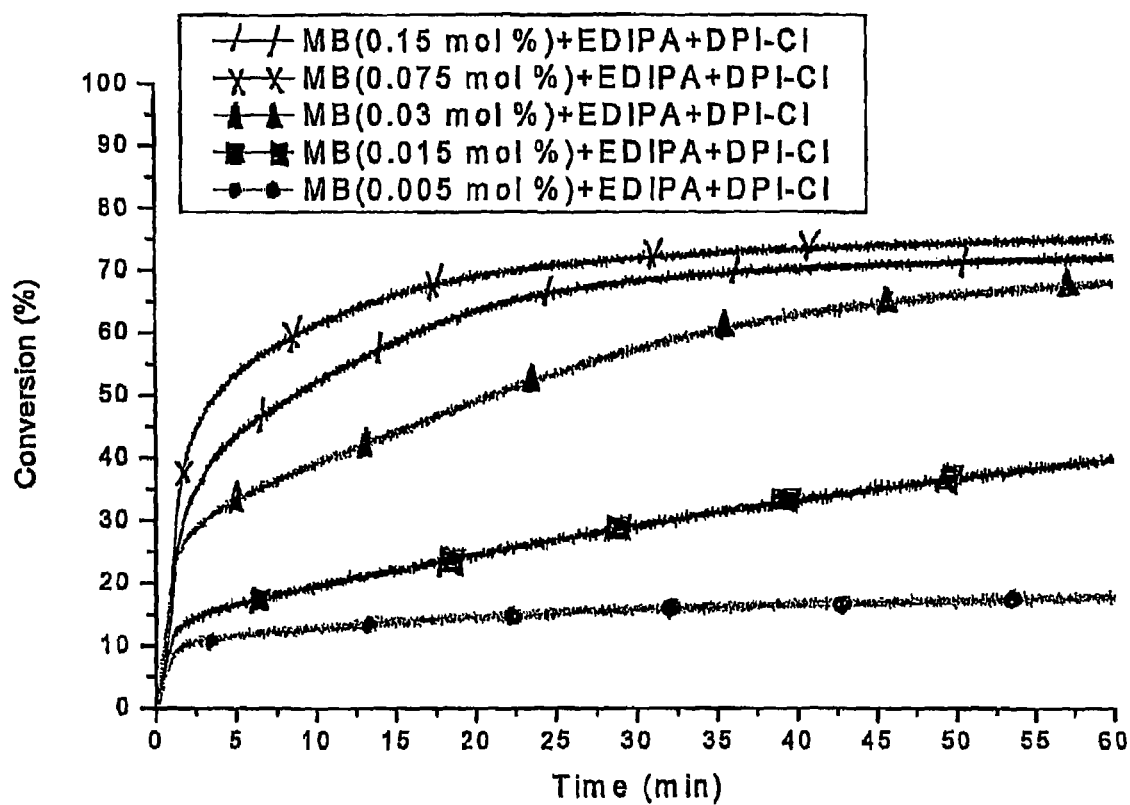
FIG. 8 illustrates the effect of varying the methylene blue (MB) concentration on polymerizable compositions of the present invention.

FIG. 8 illustrates the effect of varying the methylene blue (MB) concentration. Conversions of HEMA polymerizations as a function of illumination time with MB/EDIPA/DPI-Cl, as measured by NIR at room temperature with an incident light intensity of 500 $mW/cm^2$ and 76 second illumination time is shown. For all samples, [DPI-Cl]=0.25 mol %, [EDIPA]=3.0 mol %, and [MB]=0.005, 0.015, 0.03, 0.075 and 0.15 mol % n neat HEMA (4.122×$10^{-2}$ mol).

Example 3

Radical Dark Polymerizations: Electron Donor Effect Studies

Figure 9:
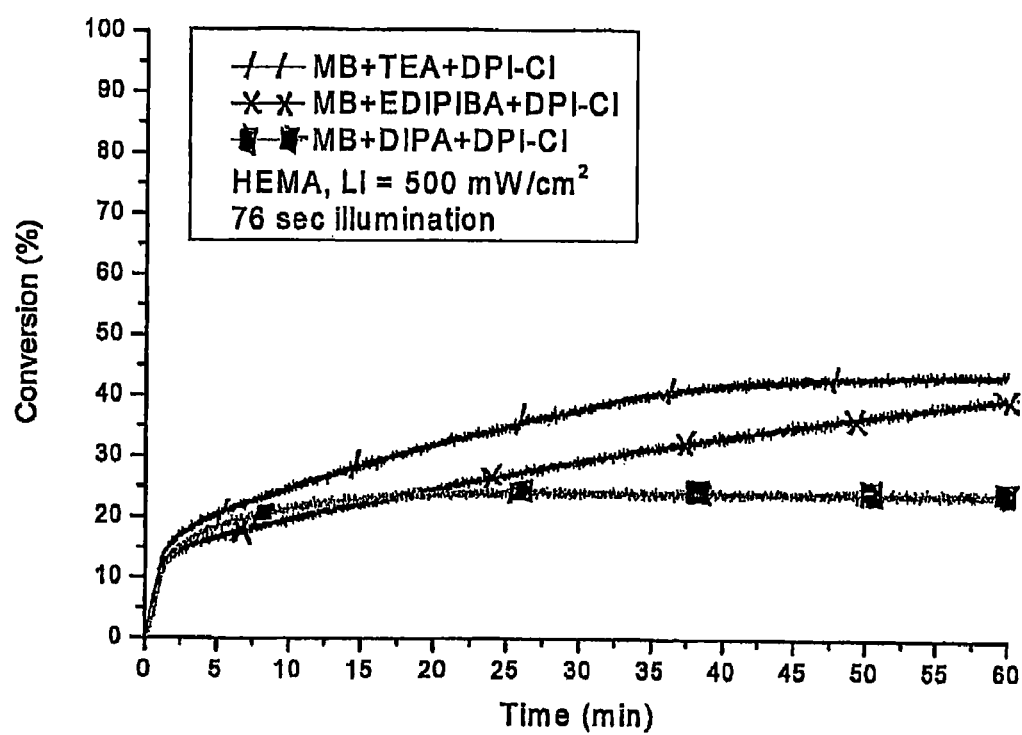
FIG. 9 illustrates the effect of varying the electron donor structure on polymerizable compositions of the present invention.

FIG. 9 illustrates the effect of varying the electron donor structure. Conversions of HEMA polymerizations as a function of illumination time with MB/DH/DPI-Cl, as measured by NIR at room temperature with an incident light intensity of 500 $mW/cm^2$ with 76 sec illumination is shown. For all samples, [MB]=0.015 mol %, [DH]=3.0 mol %, and [DPI-Cl]=0.25 mol % in neat HEMA (4.122×$10^{-2}$ mol).

Figure 10:
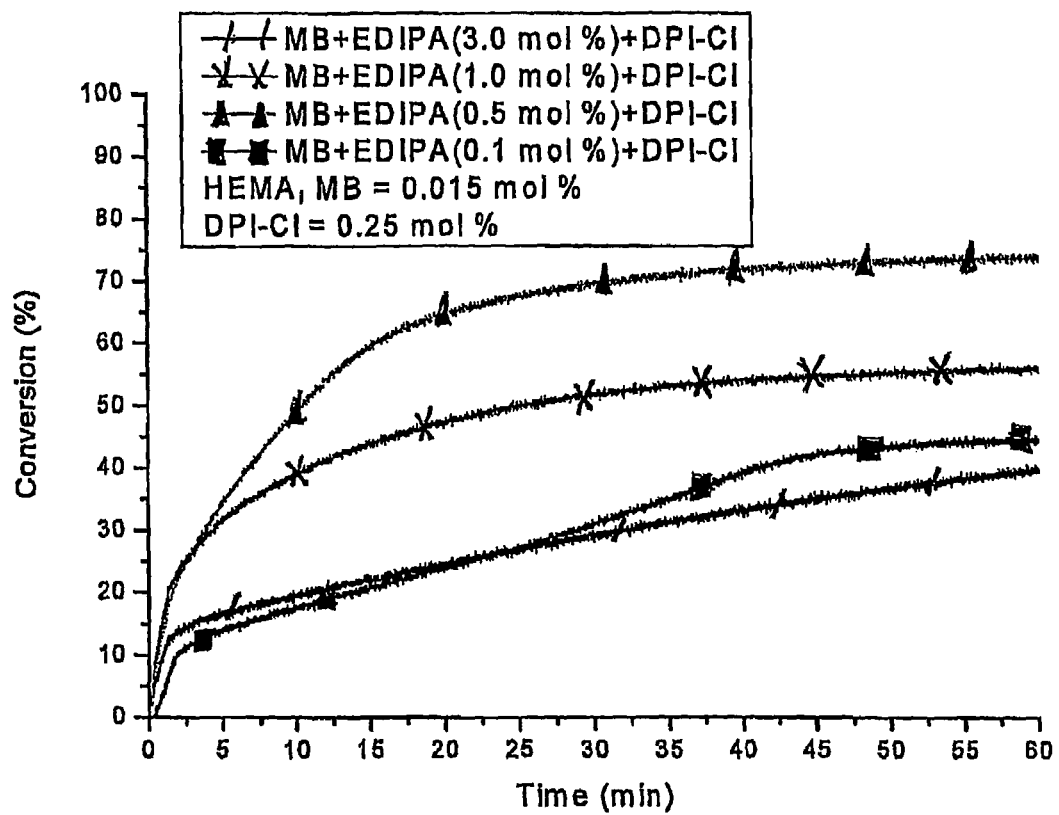
FIG. 10 illustrates the effect of varying the N-ethyl diisopropylamine on polymerizable compositions of the present invention.

FIG. 10 illustrates the effect of varying the N-ethyldiisopropylamine. Conversions of HEMA polymerizations as a function of illumination time with MB/EDIPA/DPI-Cl, as measured by NIR at room temperature with an incident light intensity of 500 $mW/cm^2$ and 76 s illumination time is shown. For all samples, [MB]=0.015 mol %, [DPI-Cl]=0.25 mol %, [EDIPA]=0.1 0.5, 1.0, and 3.0 mol % n neat HEMA (4.122×$10^{-2}$ mol).

Example 4

Radical Dark Polymerizations: Electron Acceptor Studies

Figure 11:
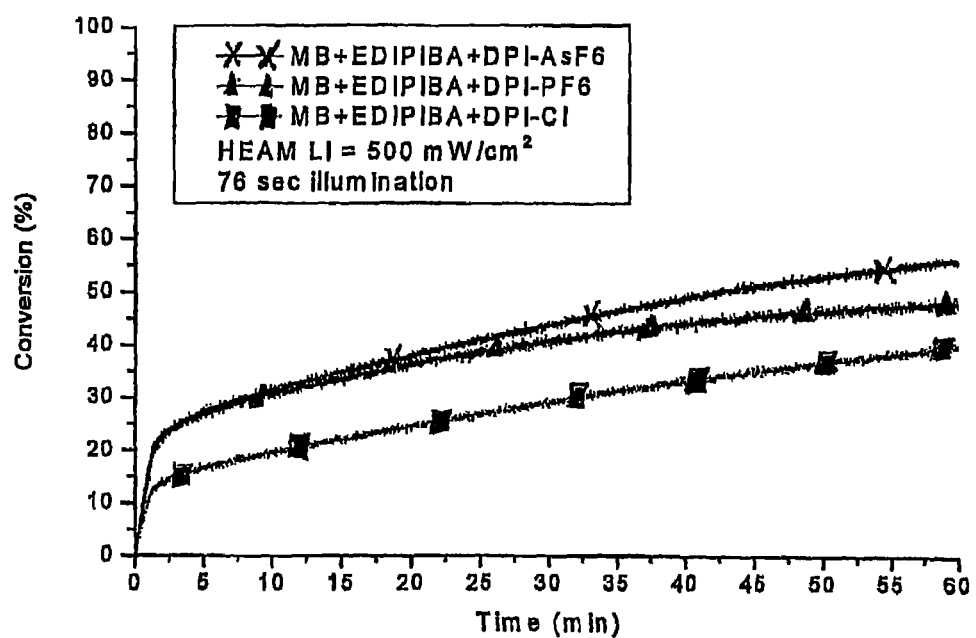
FIG. 11 illustrates the effect of varying the electron acceptor's counter anion size on the polymerizable compositions of present invention.

FIG. 11 illustrates the effect of varying the electron acceptor's counter anion size. Conversions of HEMA polymerizations as a function of illumination time with MB/EDIPIBA/DPI-Xn, as measured by NIR at room temperature with an incident light intensity of 500 $mW/cm^2$ with 76 sec illumination is shown. For all samples, [MB]=0.015 mol %, [EDIPIBA]=3.0 mol %, and [DPI-Xn]=0.25 mol % in neat HEMA (4.122×$10^{-2}$ mol).

Figure 12:
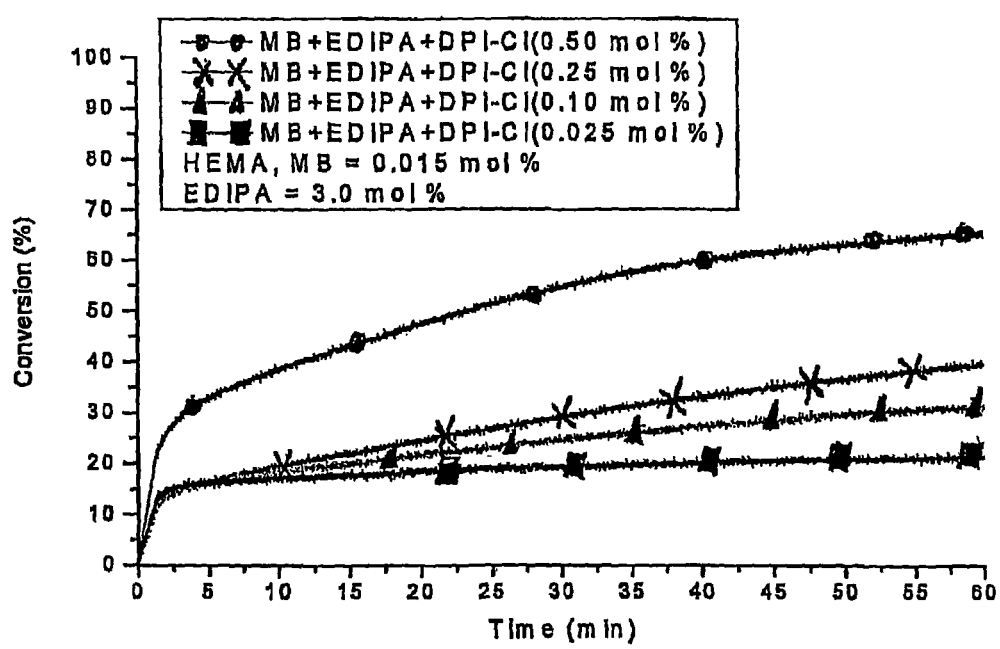
FIG. 12 illustrates the effect of varying the N,N-diisopropyl-3-pentylamine concentration on polymerizable compositions of the present invention.

FIG. 12 illustrates the effect of varying the N,N-diisopropyl-3-pentylamine concentration. Conversions of HEMA polymerizations as a function of illumination time with MB/EDIPA/DPI-Cl, as measured by NIR at room temperature with an incident light intensity of 500 $mW/cm^2$ and 76 s illumination time is shown. For all samples, [MB]=0.015 mol %, and [EDIPA]=3.0 mol %, and [DPI-Cl]=0.025, 0.10, 0.25 and 0.50 mol % in neat HEMA ($4.122 \times 10^{-2}$ mol).

Figure 13:
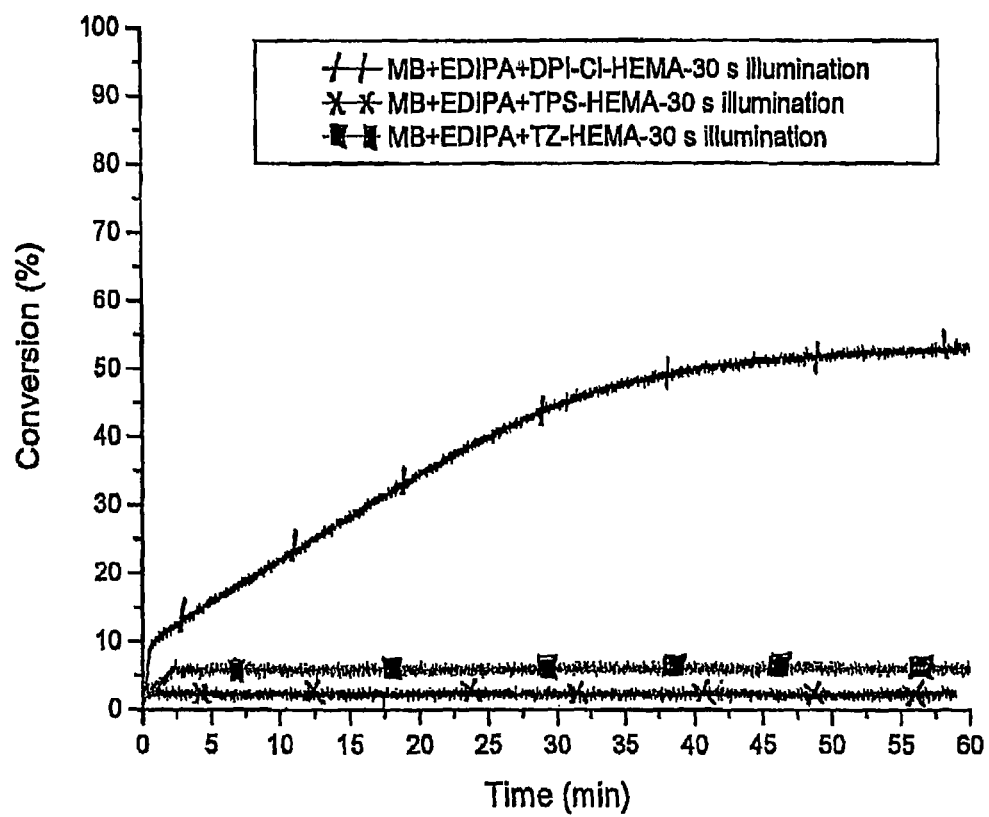
FIG. 13 illustrates the effect of varying the electron acceptor on polymerizable compositions of the present invention.

FIG. 13 illustrates the effect of varying the electron acceptor. Conversions of HEMA polymerizations with 30 s illumination MB/EDIPA/EA, as measured by NIR at room temperature with an incident light intensity of 500 mW/cm$^2$ is shown. For all samples, [MB]=0.075 mol %, and [EDIPA]=2.5 mol %, and [DPI-Cl]=[TPS]=[TZ]=0.50 mol % in neat HEMA ($4.122 \times 10^{-2}$ mol).

Example 5

Radical Dark Polymerizations: Monomer Studies

Figure 14:
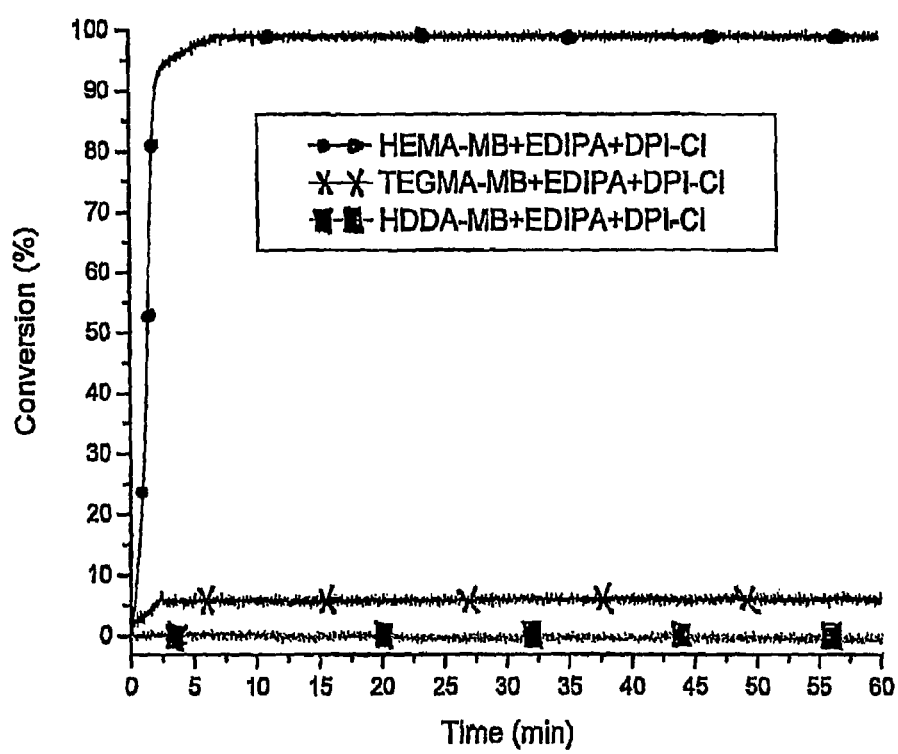
FIG. 14 illustrates the effect of varying the monomer in the on polymerizable compositions of the present invention.

FIG. 14 illustrates the effect of varying the monomer in the system. Conversions of HEMA, TEGMA and HDDA polymerizations with full illumination MB/EDIPA/EA, as measured by NIR at room temperature with an incident light intensity of 500 mW/cm$^2$ is shown. For all samples, [MB]=0.075 mol %, and [EDIPA]=2.5 mol %, and [DPI-Cl]=0.50 mol %, ([MONOMER]=$4.122 \times 10^{-2}$ mol).

Figure 15:
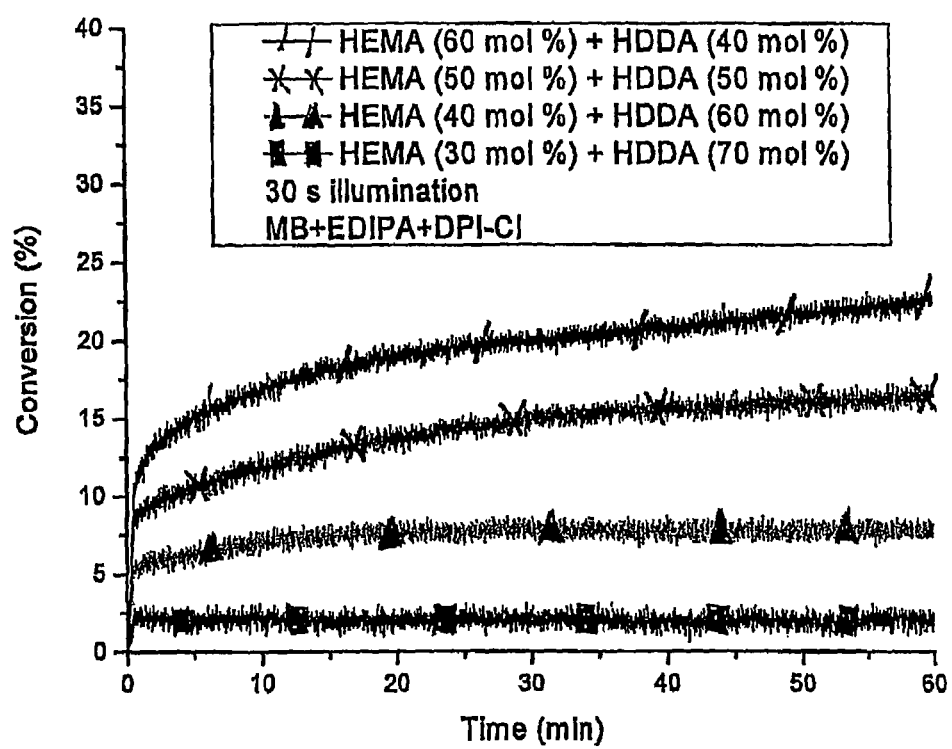
FIG. 15 illustrates the radical dark copolymerization of 2-hydroxyethyl methacrylate (HEMA) and hexanediol diacrylate (HDDA).

FIG. 15 illustrates the radical dark copolymerization of 2-hydroxyethyl methacrylate (HEMA) and hexanediol diacrylate (HDDA). Radical Dark HEMA/HDDA Copolymerizations: Conversions of HEMA/HDDA Copolymerizations with 30 s illumination time. For all samples, [MB]=0.075 mol %, [EDIPA]=2.5 mol %, and [DPI-Cl]=0.50 mol % in neat HEMA ($4.122 \times 10^{-2}$ mol) is shown.

TABLE 6

Radical Dark HEMA/HDDA Copolymerizations: Conversions of HEMA/HDDA Copolymerizations with 30 second illumination time. For all samples, [MB] = 0.075 mol %, [EDIPA] = 2.5 mol %, and [DPI-Cl] = 0.50 mol % in neat HEMA ($4.122 \times 10^{-2}$ mol).

| HEMA/HDDA (mol %) | Initial Conversion (%) | Final Conversion (%) |
|---|---|---|
| 60/40 | 9.9 | 22.6 |
| 50/50 | 28.0 | 16.4 |
| 40/60 | 5.2 | 7.4 |
| 30/70 | 2.0 | 2.0 |
| 0/100 | 0 | 0 |

Figure 16:
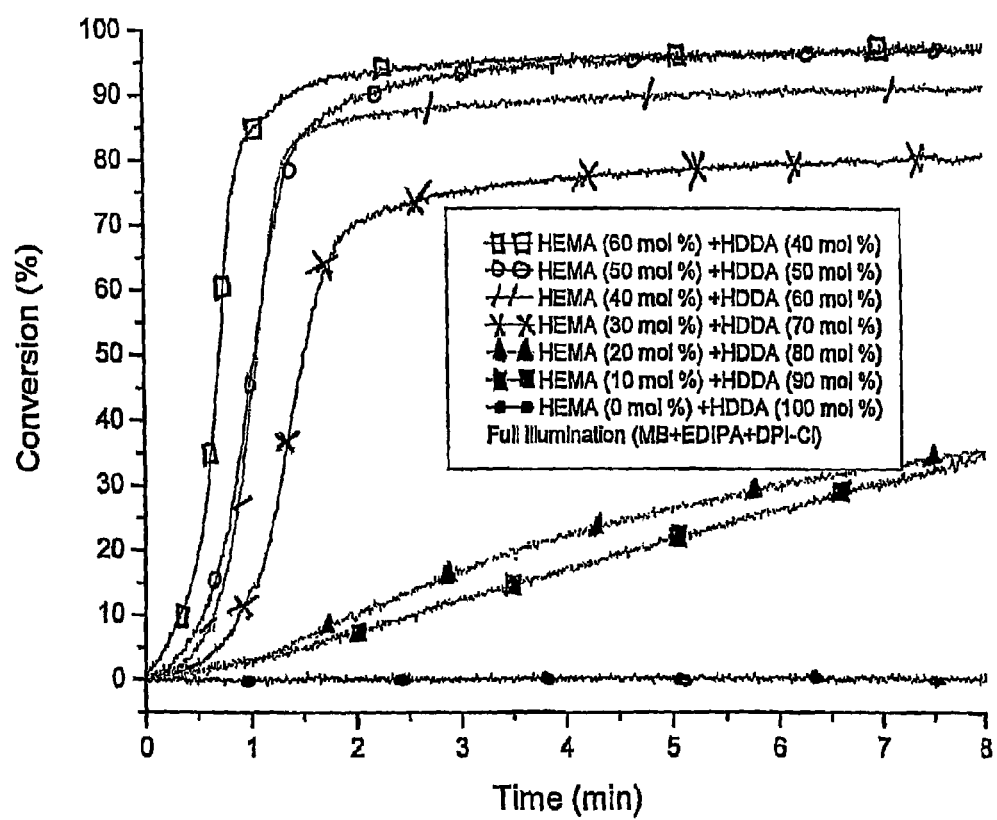
FIG. 16 illustrates the radical copolymerization of 2-hydroxyethyl methacrylate (HEMA) and 1,6-hexanediol dimethacrylate (HDDA).

FIG. 16 illustrates the radical copolymerization of 2-hydroxyethyl methacrylate (HEMA) and 1,6-hexanediol dimethacrylate (HDDA). HEMA/HDDA Radical Copolymerizations: Conversions of HEMA/HDDA Copolymerizations with full illumination time is shown. For all samples, [MB]=0.075 mol %, [EDIPA]=2.5 mol %, and [DPI-Cl]=0.50 mol % in neat HEMA ($4.122 \times 10^{-2}$ mol).

Figure 17:
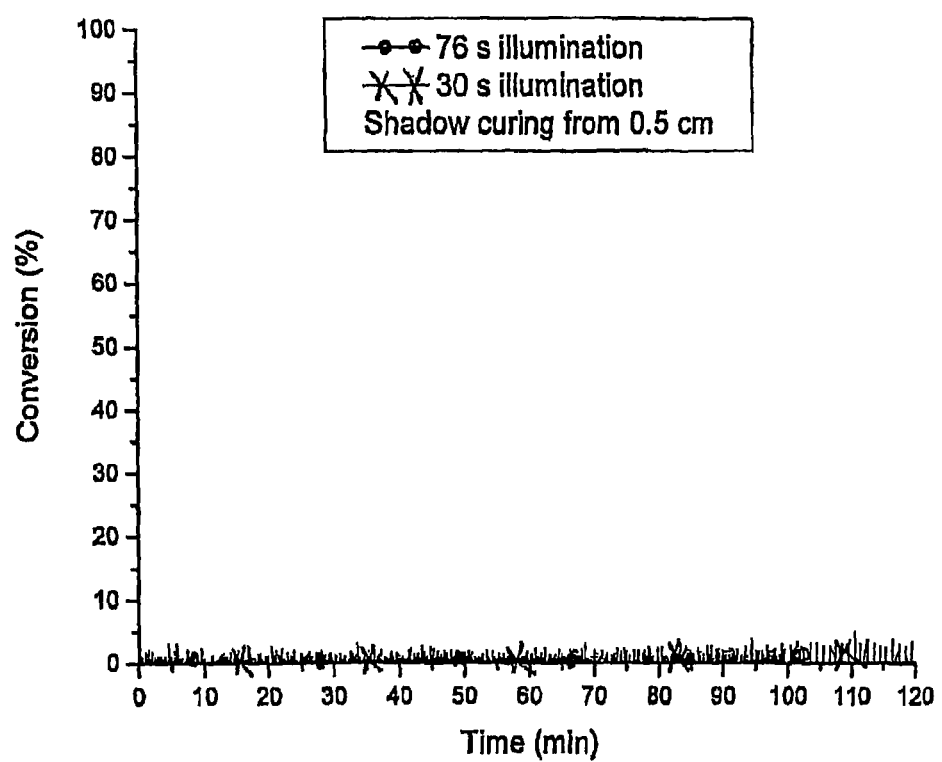
FIG. 17 illustrates the radical shadow curing of HEMA polymerization.

FIG. 17 illustrates the radical shadow curing of HEMA polymerization. Radical Shadow Curing of HEMA Polymerizations: Conversions of HEMA polymerizations as a function of illumination time with MB/EDIPA/DPI-Cl, as measured by NIR at room temperature with an incident light intensity of 500 mW/cm$^2$ at 0.5 cm with 76 s and 30 s illumination time is shown. For all samples, [DPI-Cl]=0.25 mol %, [EDIPA]=3.0 mol %, and [MB]=0.005, 0.015, 0.03, 0.075 and 0.15 mol % n neat HEMA ($4.122 \times 10^{-2}$ mol).

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described herein above are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A dark curing polymerizable composition comprising:
   a. a monomer with at least one abstractable hydrogen selected from the group consisting of 2-hydroxyethyl acrylate (HEA), 2-hydroxyethyl methacrylate (HEMA), acrylamide, methacrylamide, bisGMA {2,2-bis[4-(2-hydroxy-3-methacryloxyprop-1-oxy)phenyl]propane}, urethane dimethacrylate, glycerol monomethacrylate, 1,3-glycerol dimethacrylate, tetrahydrofurfuryl methacrylate, 1,6-hexanediol diacrylate, 1,6-hexanediol dimethacrylate (HDDA), methacrylic acid, triethylene glycol dimethacrylate, styrene, and neodecyl vinyl ester; and
   b. a three-component initiator system, soluble in said monomer, comprising:
      i. methylene blue;
      ii. an electron donor selected from the group consisting of N,N-diisopropyl-3-pentylamine, N-ethyldiisopropylamine, and 1,2,2,6,6-pentamethylpiperidine; and
      iii. an electron acceptor selected from the group consisting of ferrocenium hexafluorophosphate, diphenyliodonium hexafluoroarsenate, [4-[(2-hydroxytetradecyl)oxyl]phenyl]phenyliodonium hexafluoroantimonate, diphenyliodonium hexafluorophosphate, 2,4,6-tris(trifluoromethyl)-1,3,5-triazine, diphenyl iodonium chloride and diphenyl iodonium tetrafluoroborate.

2. A method for dark curing polymerization, comprising initiating polymerization in a dark curing polymerizable composition of claim 1, using a visible-light source; removing the visible light source to allow polymerization to cure under dark conditions.

3. A dark curing polymerizable composition comprising $4.122 \times 10^{-2}$ mol. (neat) of an acrylate selected from the group consisting of 2-hydroxyethyl acrylate and 2-hydroxyethyl methacrylate, and a three-component initiator system comprising methylene blue, N-ethyldiisopropylamine; and diphenyliodonium chloride.

4. The dark curing polymerizable composition of claim 3, wherein the acrylate is 2-hydroxyethyl methacrylate and the three-component initiator system comprises 0.075 mol % methylene blue; 2.5 mol % N-ethyldiisopropylamine; and 0.5 mol % diphenyliodonium chloride, dissolved in said 2-hydroxyethyl methacrylate.

5. The dark curing polymerizable composition of claim 3, wherein the acrylate is 2-hydroxyethyl acrylate and the three-component initiator system comprises 0.015 mol % methylene blue; 3.0 mol % N-ethyldiisopropylamine; and 0.25 mol % diphenyliodonium chloride, dissolved in said 2-hydroxyethyl acrylate.

6. The dark curing polymerizable composition of claim 1, wherein the electron donor is selected from the group consisting of N-ethyldiisopropylamine, and N,N-diisopropyl-3-pentylamine.

7. The dark curing polymerizable composition of claim 1, wherein the monomer is selected from the group consisting of 2-hydroxyethyl acrylate (HEA), 2-hydroxyethyl methacrylate (HEMA), and glycerol monomethacrylate.

* * * * *